United States Patent
Klein

(10) Patent No.: US 9,267,870 B2
(45) Date of Patent: Feb. 23, 2016

(54) CONSTANT FORCE COMPRESSION TOOL

(71) Applicant: Allosource, Centennial, CO (US)

(72) Inventor: Raymond J. Klein, Centennial, CO (US)

(73) Assignee: Allosource, Centennial, CO (US)

( * ) Notice: Subject to any disclaimer, the term of this patent is extended or adjusted under 35 U.S.C. 154(b) by 489 days.

(21) Appl. No.: 13/746,929

(22) Filed: Jan. 22, 2013

(65) Prior Publication Data

US 2013/0186206 A1 Jul. 25, 2013

Related U.S. Application Data

(60) Provisional application No. 61/589,220, filed on Jan. 20, 2012.

(51) Int. Cl.
*G01N 3/08* (2006.01)
*G01F 19/00* (2006.01)

(52) U.S. Cl.
CPC *G01N 3/08* (2013.01); *G01F 19/00* (2013.01); *G01F 19/007* (2013.01)

(58) Field of Classification Search
CPC .............. A24F 9/00; A24F 9/02; G01N 3/08
USPC ............................................................ 73/818
See application file for complete search history.

(56) References Cited

U.S. PATENT DOCUMENTS

| | | | | |
|---|---|---|---|---|
| 2,561,266 A | * | 7/1951 | Dietert | 264/40.5 |
| 4,206,770 A | | 6/1980 | Ozgener | |
| 6,086,594 A | * | 7/2000 | Brown | 606/92 |
| 7,448,264 B2 | * | 11/2008 | Boyce | 73/172 |

* cited by examiner

*Primary Examiner* — Max Noori
*Assistant Examiner* — Octavia Hollington
(74) *Attorney, Agent, or Firm* — James A. Sheridan; Sheridan Law, LLC

(57) ABSTRACT

There is disclosed a constant force compression tool for measuring a compressible material. In an embodiment, the tool includes a handle having a passageway receiving a plunger. The tool includes a biasing member in communication with the plunger and the handle. The tool includes a retaining element in communication with the plunger and the handle. There is disclosed a system for measuring a compressible material with a measurement tube and a constant force compression tool. There is disclosed a method of measuring a compressible material. In an embodiment, the method includes selecting a measurement tube. The method includes placing a compressible material into the measurement tube. The method includes pressing a plunger against the compressible material. The method includes monitoring an indicator to determine a full volume of compressible material between the end of the plunger and the conical tube. Other embodiments are also disclosed.

15 Claims, 19 Drawing Sheets

CONSTANT FORCE COMPRESSION TOOL

REFERENCE TO PENDING PRIOR PATENT APPLICATION

This patent application claims the benefit under 35 U.S.C. 119(e) of U.S. Provisional Patent Application No. 61/589,220, filed Jan. 20, 2012, by Raymond J. Klein for "CONSTANT FORCE COMPRESSION TOOL," which patent application is hereby incorporated herein by reference.

BACKGROUND

Generally, ground cancellous bone material is measured by scooping the material into a measurement tube followed by tamping the material with a solid rod. The amount of compression may vary due to different force amounts exerted by the users. The material expands after transfer from the measurement tube to the jar for distribution. This results in the packaging and distribution of an inconsistent amount of material that may or may not meet advertised amounts.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is provided a constant force compression tool for measuring a compressible material, the tool comprising: a plunger having a first end and a second end in opposition to one another, the first end having a surface configured to compress the compressible material; a handle having a passageway receiving the plunger between the first end and the second end; a biasing member in communication with the plunger and the handle so as to provide a biasing force between the plunger and the handle; and a retaining element in communication with the plunger and the handle so as to prevent the plunger from disengagement with the handle.

In another embodiment, there is provided a system for measuring a compressible material, the system comprising: a measurement tube having a sidewall extending between a closed end and an open end; and a constant force compression including: a plunger having a first end and a second end in opposition to one another, the first end having a surface configured to compress the compressible material, and the second end having a ring configured to identify an appropriate measured volume of the compressible material, wherein the first end has a diameter and a length configured for disposition into the measurement tube through the open end toward the closed end; a handle having a passageway receiving the plunger between the first end and the second end, and a portion to index the ring of the plunger, wherein the handle has a stop sized to rest against the open end of the measurement tube; a biasing member in communication with the plunger and the handle so as to provide a biasing force between the plunger and the handle, wherein the spring has a fully compressed configuration extending the first end of the plunger an appropriate distance toward the closed end of the measurement tube so as to provide a predetermined amount of space within the measurement tube between the first end of the plunger and the closed end of the measurement tube; and a retaining element in communication with the plunger and the handle so as to prevent the plunger from disengagement with the handle.

In yet another embodiment, there is provided a method of measuring a compressible material, the method comprising selecting a measurement tube; placing a compressible material into the measurement tube; pressing a plunger of a constant force compression tool to dispose an end against the compressible material; and monitoring an indicator to determine if the plunger is disposed at a predefined distance within the conical tube together with a full volume of compressible material between the end of the plunger and the conical tube.

Other objects, features, and advantages of the invention will become apparent from the following detailed description of the invention with reference to the accompanying drawings.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Figure 1:
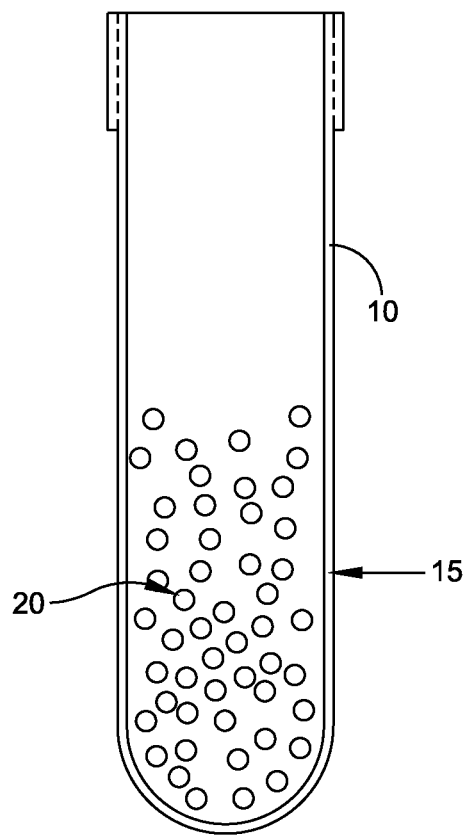
FIG. 1 illustrates an existing measurement tube.

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

In an embodiment, there is provided a multiple piece tamp rod 25 to insure a standard force or pressure is applied at a prescribed cancellous measurement. This multiple piece tamp rod 25 is referred to herein as a constant force compression tool 25 and includes a measurement tube 10 as well as the tamp rod 30 or plunger 30. The constant force compression tool 25 allows a user, such as a technician, to apply a consistent pressure, or load, to a material 20. The multiple piece tamp rod 25 further allows the user to deliver consistently measured and uniformly compressed materials 20. Measuring a compressible material 20 with a consistent pressure, or load, ensures that the distributed material 20 is provided in a consistent volume in each container.

The constant force compression tool 25 measures a consistent volume of compressible material 20. In one embodiment, the constant force compression tool measures 25 ground cancellous bone used in tissue banking manufacturing. Cancellous bone is compressible and occupies a different volume space depending upon the applied amount of force/ pressure. It is important that the volume of the product measured is accurate so that the end user (e.g., a surgeon) will have the appropriate amount of material 20 available for use (e.g., planned spinal fusion surgery). The constant force compression tool 25 may be utilized in other industries/materials to consistently measure compressible materials 20.

Figure 2:
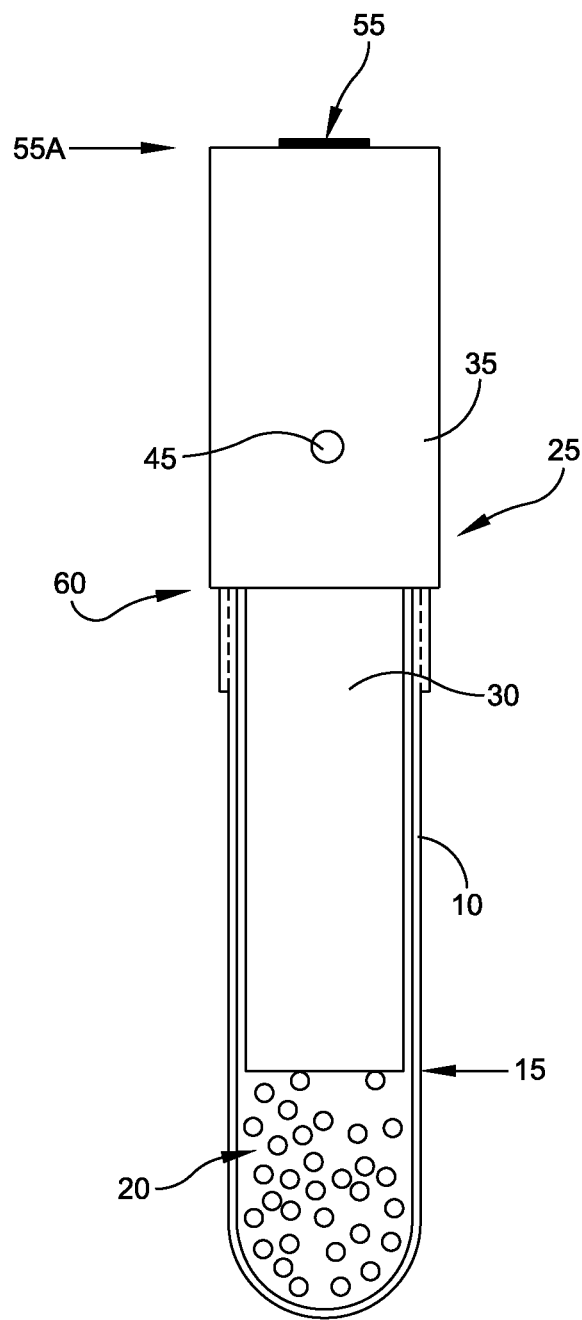
FIGS. 2-4 illustrate an exemplary embodiment of a constant force compression tool used in tandem with an existing measurement tube.
Figure 3:
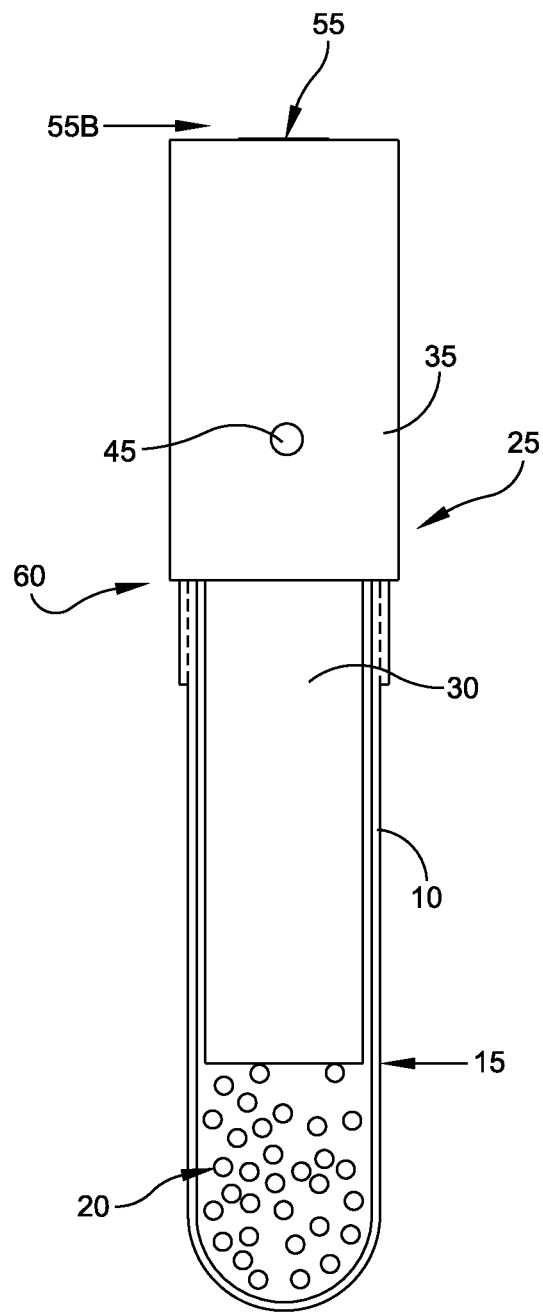
Figure 4:
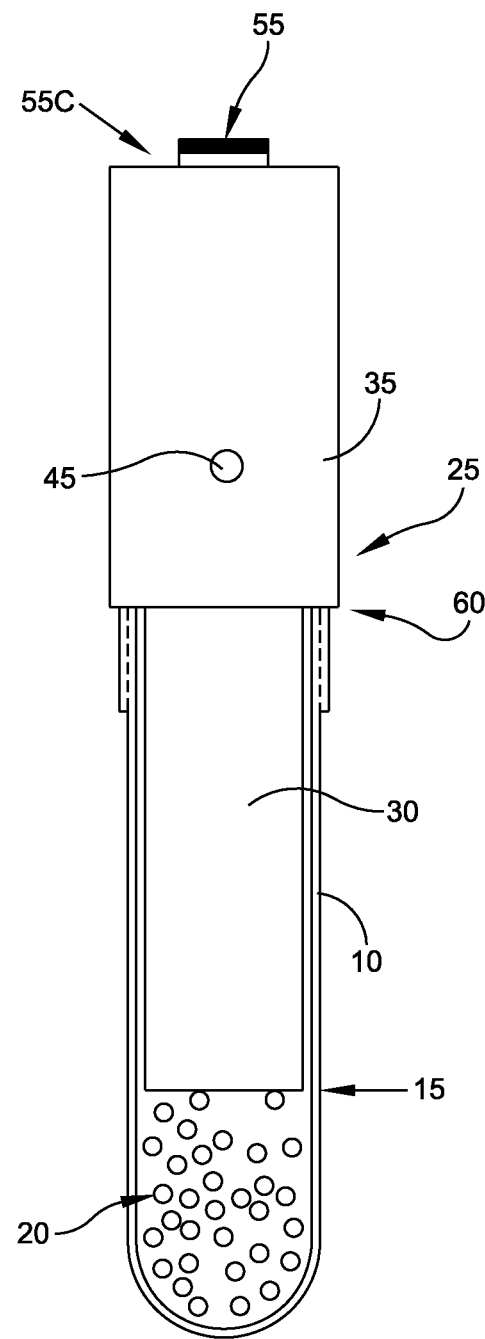

The constant force compression tool 25 may be used in tandem with existing measurement tubes 10 (see FIG. 1.) The size of the plunger 30, the handle 35, and the spring 40 the tool 25 may be configured to coordinate with the size of the measurement tube 10 so that for a particular volume the plunger 30 on the tool 25 aligns with the prescribed volume 15 and provides the desired compressive force/pressure to the material 20 being measured. FIGS. 2-4 illustrate an exemplary embodiment of the constant force compression tool 25 used in tandem with an existing measurement tube 10.

Figure 5:
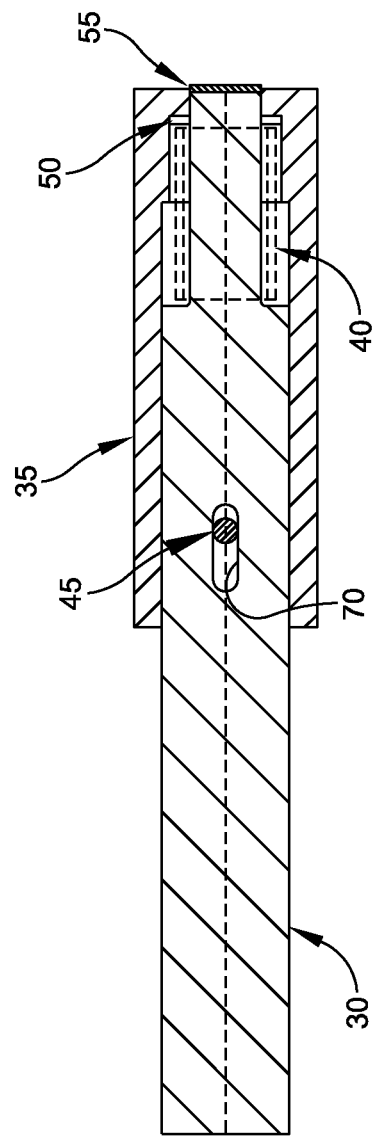
FIG. 5 illustrates a schematic embodiment of a constant force compression tool.
Figure 6:
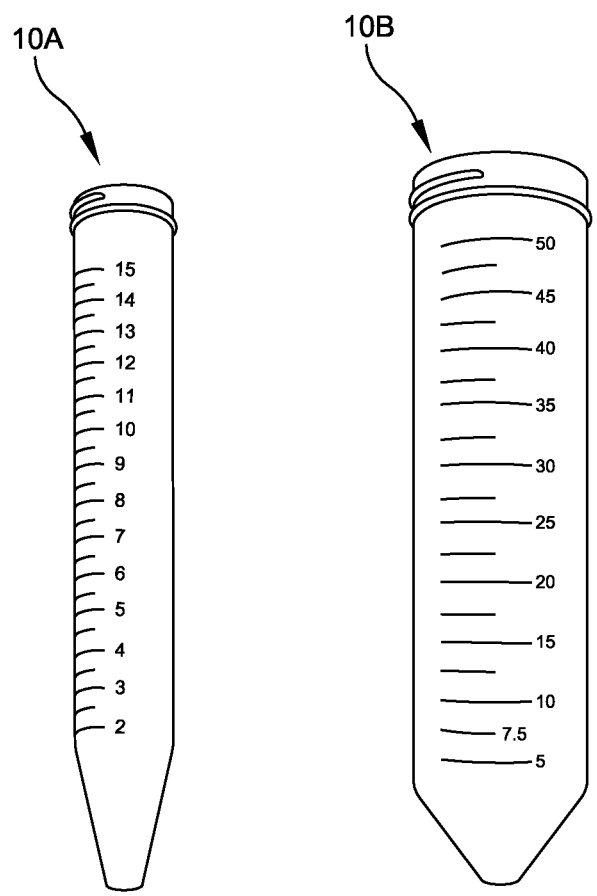
FIG. 6 illustrates two examples of measurement tubes.
Figure 7:
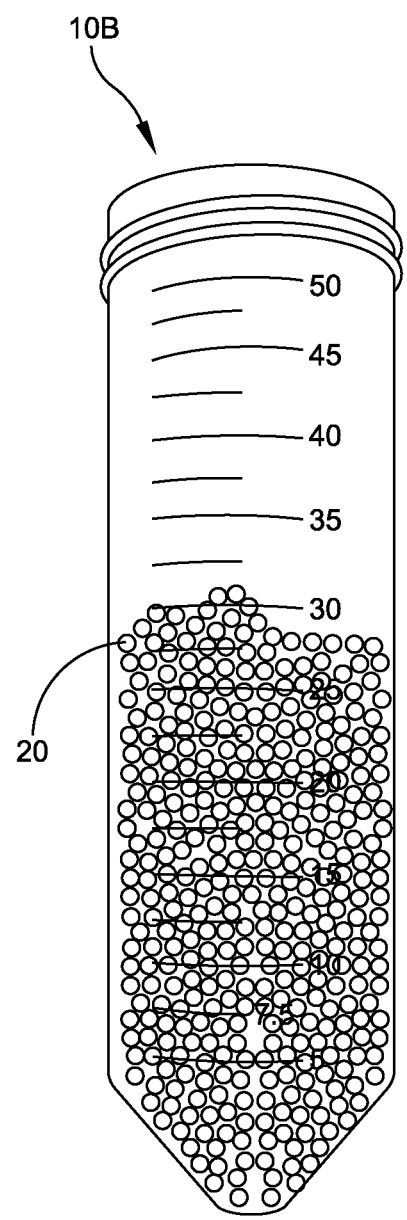
FIG. 7 illustrates compressible material disposed in a measurement tube.
Figure 8:
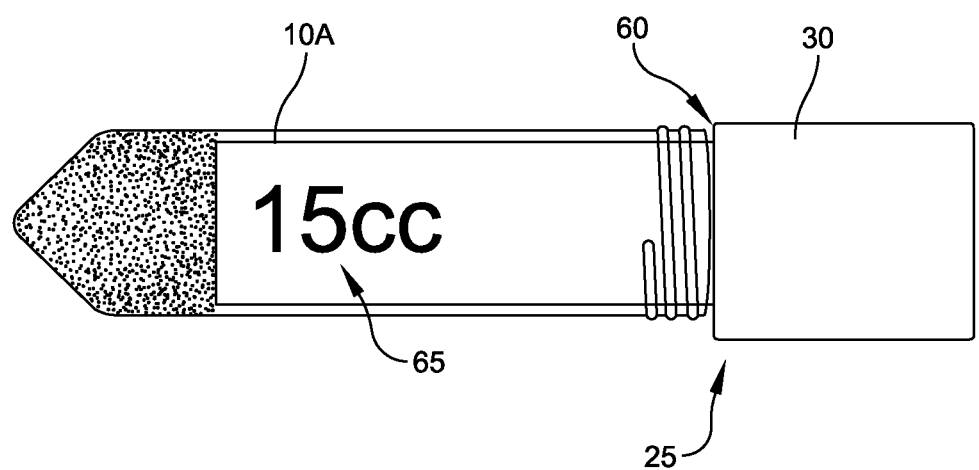
FIGS. 8-11 illustrate various features of a constant force compression tool with respect to an exemplary method of measuring a compressible material.
Figure 9:
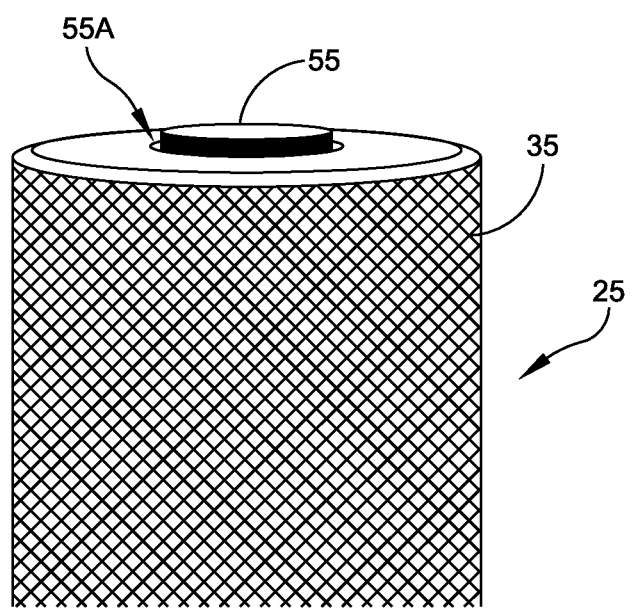
Figure 10:
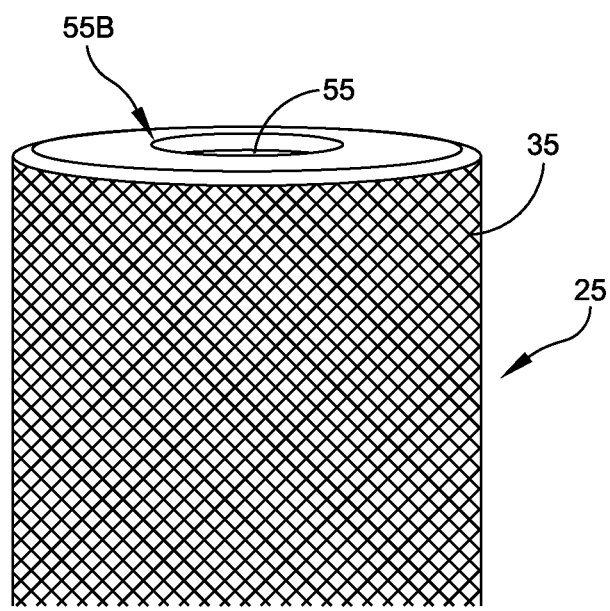

With reference to FIG. 5, the constant force compression tool 25 may include a plunger 30, handle 35, spring 40, retaining pin 45, and one or more shims 50. However, one or more of these features may be omitted or modified.

The plunger 30 may perform several functions. The plunger 30 may provide surface to compress the material 20 being measured. The plunger 30 may react with the force supplied by the spring 40 to transmit this force/pressure to the material 20 being compressed. The plunger 30 may provide a contrasting ring 55 to identify when the material 20 being measured is the appropriate height or if material needs to be added or subtracted. The plunger 30 may allow limited movement with the slot 70 provided that interacts with the retaining pin 45.

The handle 35 may perform several functions. The handle 35 may react with the force supplied by the spring 40 to transmit this force to the plunger 30. The handle 35 may provide a contrasting surface 55A, 55B, 55C with the plunger ring 55 to identify when the material 20 being measured is the appropriate height or if material needs to be added or subtracted. The handle 35 may hold the retaining pin 45. The handle 35 may provide a knurled surface for the user to hold onto the device 25.

The spring 40 may compress to provide the force exerted by the plunger 30.

The retaining pin 45 may limit the motion of the plunger 30 relative to the handle 35 and keeps the tool assembly 25 together.

One or more shims 50 may be added to adjust the spring force for each particular tool assembly 25. The height of the shims 50 may be modified to account for variation in plunger 30, handle 35 and spring 40 tolerances.

For a manual operation, an embodiment of the constant force compression tool 25 may be used in tandem with existing measurement tubes 10. As described above, the tool 25 is sized so that for a particular volume the plunger 30 on the tool 25 aligns with the prescribed volume and provides the desired compressive force/pressure to the material 20 being measured.

In another embodiment, the constant force compression tool 20 may include a custom manufactured measuring receptacle to optimize to the geometry of the measuring receptacle if needed. The geometry of this receptacle may be configured in a manner to ensure consistent compression of the material being used for the volume required. For example a "short" column of material may tend to be compressed more than a "tall" column of material depending upon the material properties.

Another embodiment of the constant force compression tool 25 may provide a sensor with feedback (e.g., visual, auditory, or a combination of both) to identify whether there is a correct amount of material 20, too little material 20, or too much material 20.

Another embodiment may utilize feature of the constant force compression tool 25 in an automated or semi-automated piece of equipment to perform some of the manual functions, such as adding or removing material 20.

A primary use of the constant force compression tool 25 includes providing a consistent volume measurement of compressible materials 20. Another primary use of the constant force compression tool 25 includes reduction of the variance between human users for volume measurements.

The constant force compression tool 25 provides a method of volume measurement that eliminates the variation of force applied between different users. The constant force compression tool 25 may be used in conjunction with a measurement device 10 using visual volume graduation on the device. In an embodiment, an indicator 65 may be used on the tool 25 itself to eliminate the need for visual graduations on the measurement device 10.

The constant force compression tool 25 may be constructed of lightweight materials to allow for easy handling. This may include different plastics, aluminum or titanium.

For aseptic applications where the constant force compression tool needs to be steam sterilized, materials that are capable of handling higher temperatures are used. Materials with similar coefficients of thermal expansion are used to prevent potential damage during thermal cycling. These may include plastics such as polysulfone, polyetherimide, polyether ether ketone or polyphenylsulfone.

The constant force compression tool 25 may be assembled with the spring 40 installed into the handle 35. The plunger 30 may be installed with the smaller diameter into the spring 40/handle 35. The intermediate assembly may be compressed until the indicator line on the plunger aligns with the top of the handle 35. If the indicator line 55 is not being used, then the distance the plunger protrudes from the handle is obtained. The intermediate assembly of tool 25 (which does not include tube 10) is placed into a load measurement device to determine if the desired force is obtained. If the force is not adequate, then one or more shims 50 may be installed and the process is repeated until the desired force is obtained. Next, the retaining pin 45 may be installed into the handle 35.

Use of the constant force compression tool 25 as a manual tool may be limited to applications where the force applied is within human capabilities to apply that force. A machine with higher capabilities may be required for application of higher amounts of force.

The constant force compression tool 25 may be used for measurement of other materials where constraints as listed above are described. Some potential users include tissue banks that process musculoskeletal tissues. Other users may include industries where consistent measurement of compressible materials is required (e.g., tea measurement.) Monitoring of production results provides more accuracy than other measurement tools for compressible materials.

With reference to FIGS. 6-10, an exemplary embodiment of measurement is described. Select the appropriate measurement tube 10 (e.g., 15 ml tube 10A for smaller volumes, 50 ml tube 10B for larger volumes, etc.). (See FIG. 6.)

Using the measurement tube 10, scoop ground cancellous bone material 20 (referred to herein as "cancellous") into tube 10B so the loose amount is more than the targeted tamp amount. (See FIG. 7.)

Using the appropriate size spring-loaded tamp tool 25 (with a size indicator 65) press the plunger against the cancellous until the handle 10 of the tamp tool contacts the end of the tube 10A at contact 60. (See FIG. 8.)

Under adequate lighting, with the end of the tamp tool 25 rotated slightly to view the measurement ring 55, determine the location of the ring 55 and proceed as follows:

1) If the measurement ring 55 protrudes and aligns (at position 55A) with the end of the handle 35 proceed to package the appropriately measured amount of cancellous 20. (See FIG. 9.)

2) If the measurement ring 55 is below (at position 55B) the end of the handle 35, add more cancellous 20 and re-tamp. (See FIG. 10.)

Figure 11:
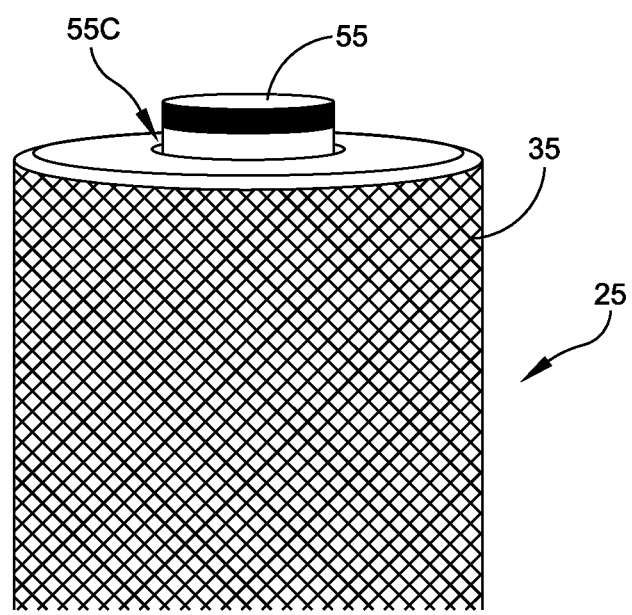

3) If the measurement ring 55 protrudes (at position 55C) from the handle 35 and white material is showing below the ring 55, remove some cancellous 20 and/or re-tamp. (See FIG. 11.)

In one embodiment, the technician should not tamp the same cancellous 20 more than three (3) times. If three tamps are performed and the black ring 55 is not aligned, the technician may remove the cancellous 20 from the tube 10 and start over.

In one embodiment, the black ring 55 on the tool 25 is used for volume measurement rather than graduations on the tube.

Figure 12:
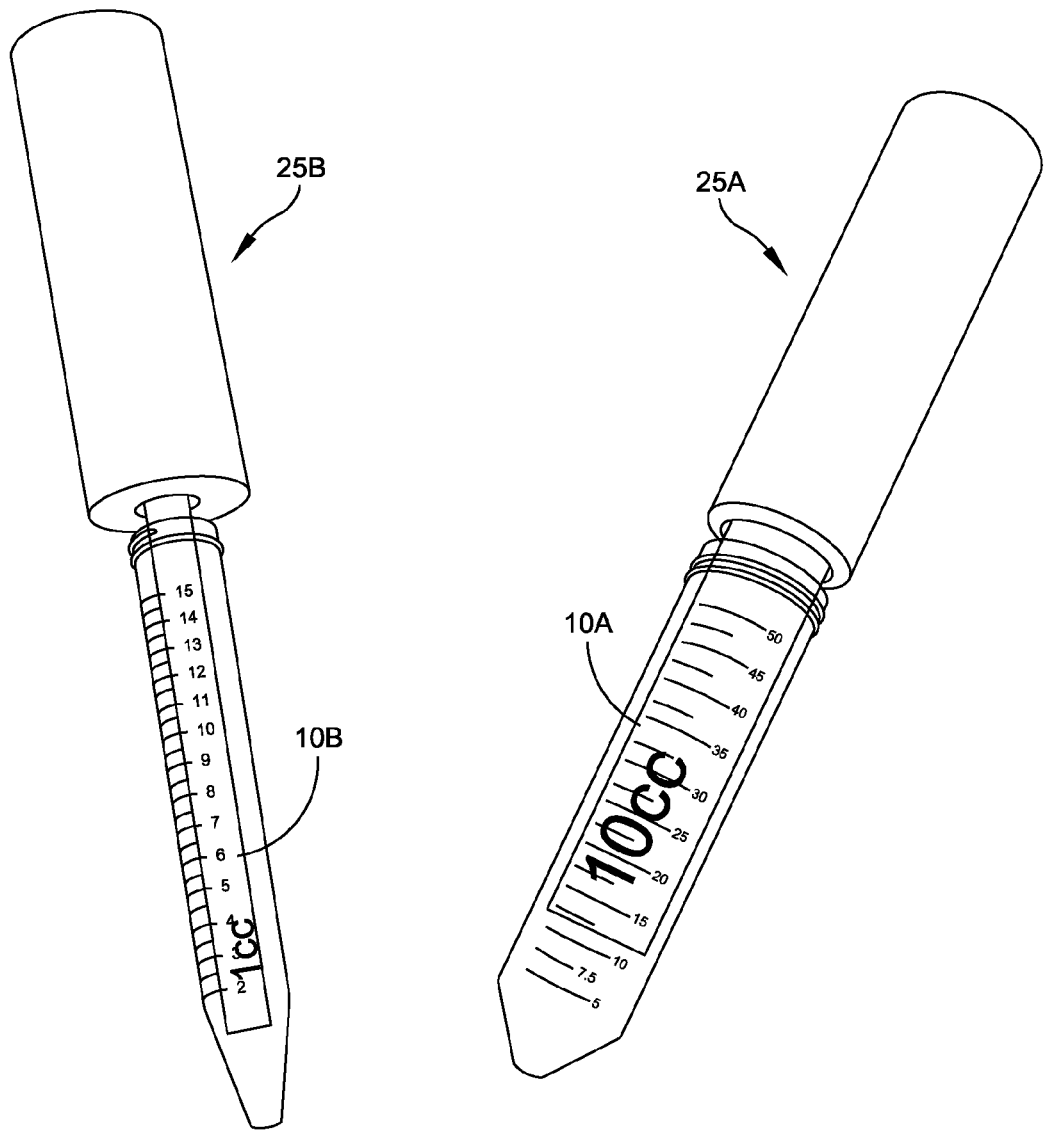
FIGS. 12-14, 15A-15C, 16A-16C, 17A, 17B, 18A-18C, and 19A-19C illustrate various embodiments and components of a constant force compression tool.
Figure 13:
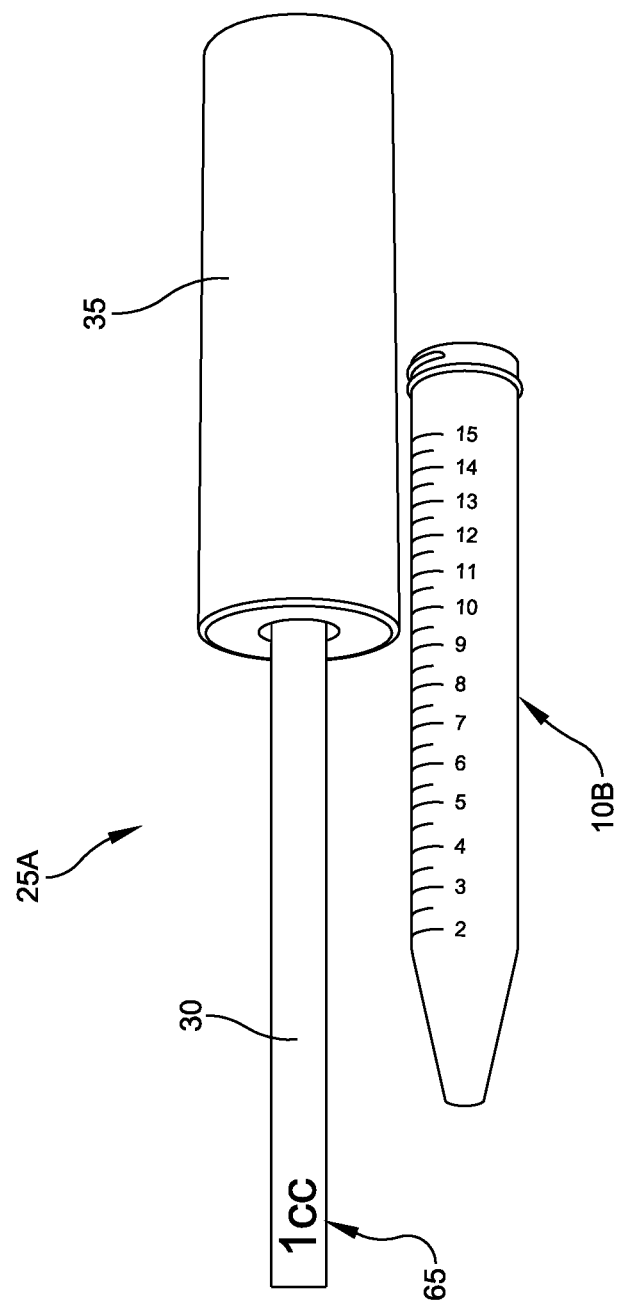

FIG. 12 illustrates two exemplary embodiments of small tube 10A configured to measure compressible material together with small tool 25A and large tube 10A configured to measure compressible material together with large tool 25A. FIG. 13 illustrates small tube 10A and small tool 25B separated from one another.

Figure 14:
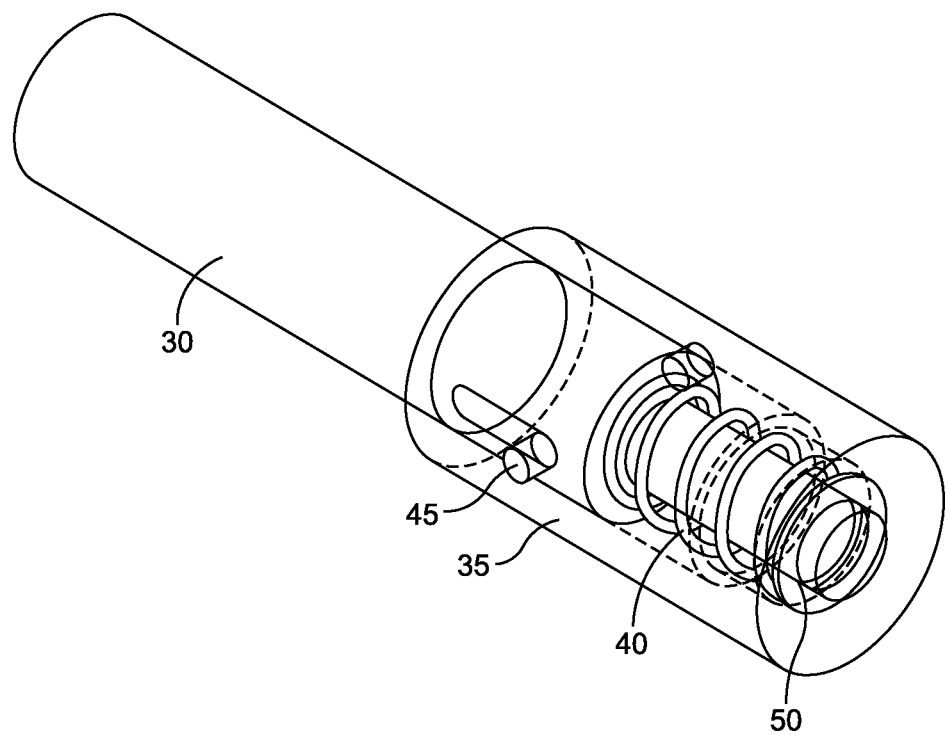
Figure 14:
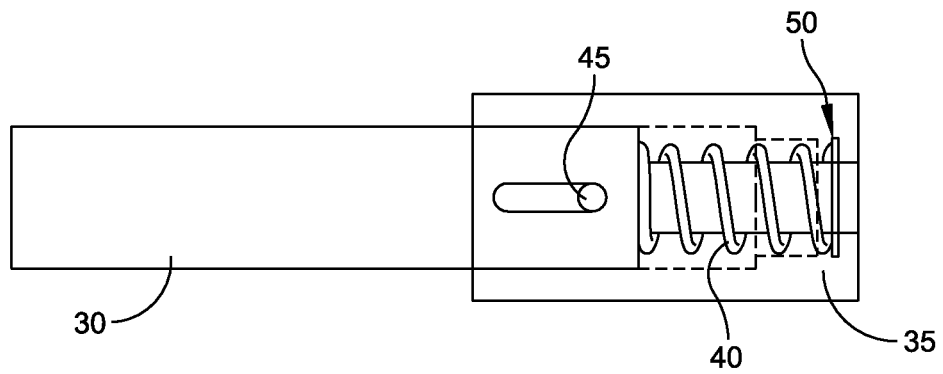
Figure 15A:
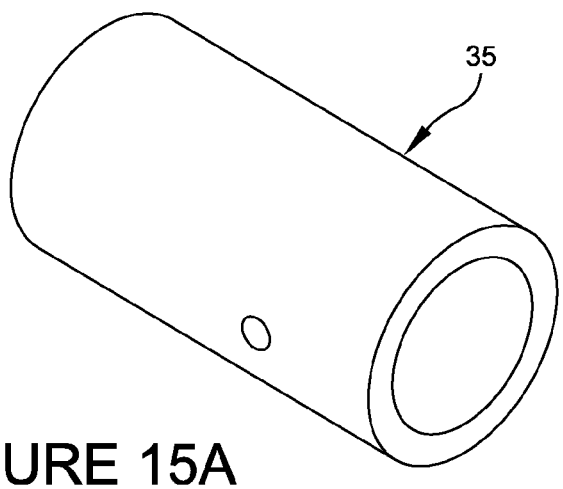
Figure 15B:
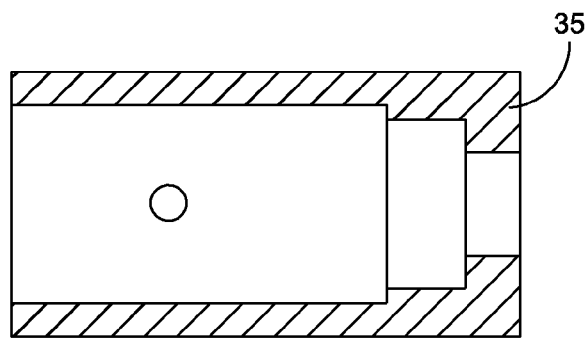
Figure 15C:
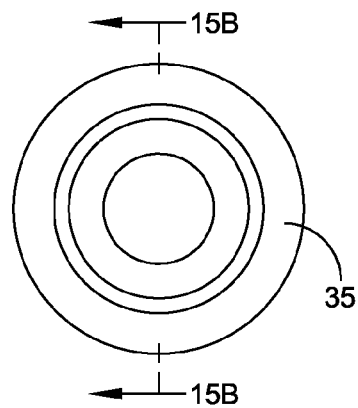
Figure 16A:
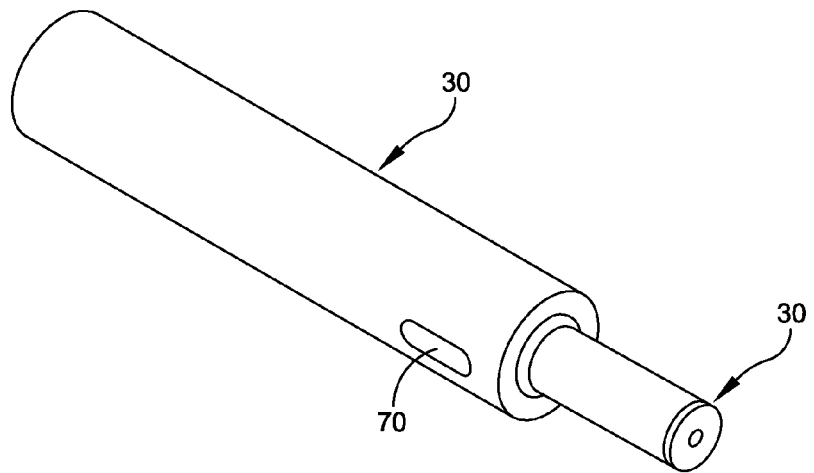
Figure 16B:
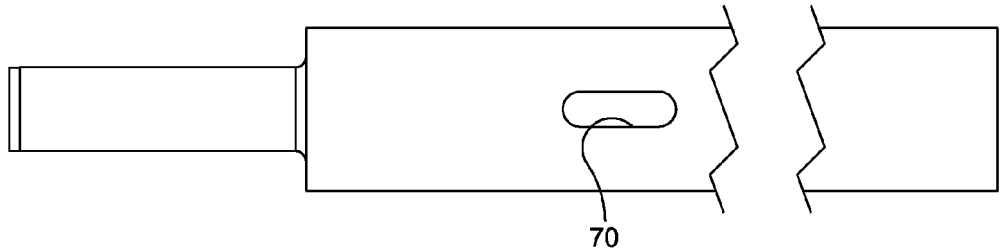
Figure 16C:
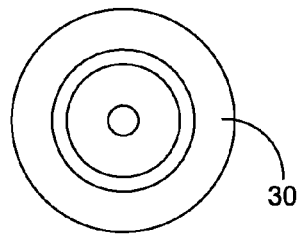

FIG. 14 is a schematic illustration of an exemplary embodiment plunger 30, handle 35, spring 40, retaining pin 45, and shim 50. FIGS. 15A-15C illustrate various views of an exemplary embodiment of handle 35. FIGS. 16A-16C illustrate various views of an exemplary embodiment of plunger 30.

Figure 17A:
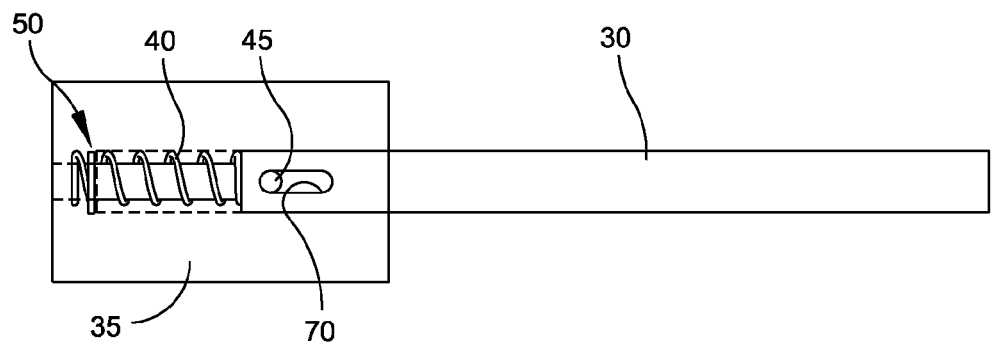
Figure 17B:
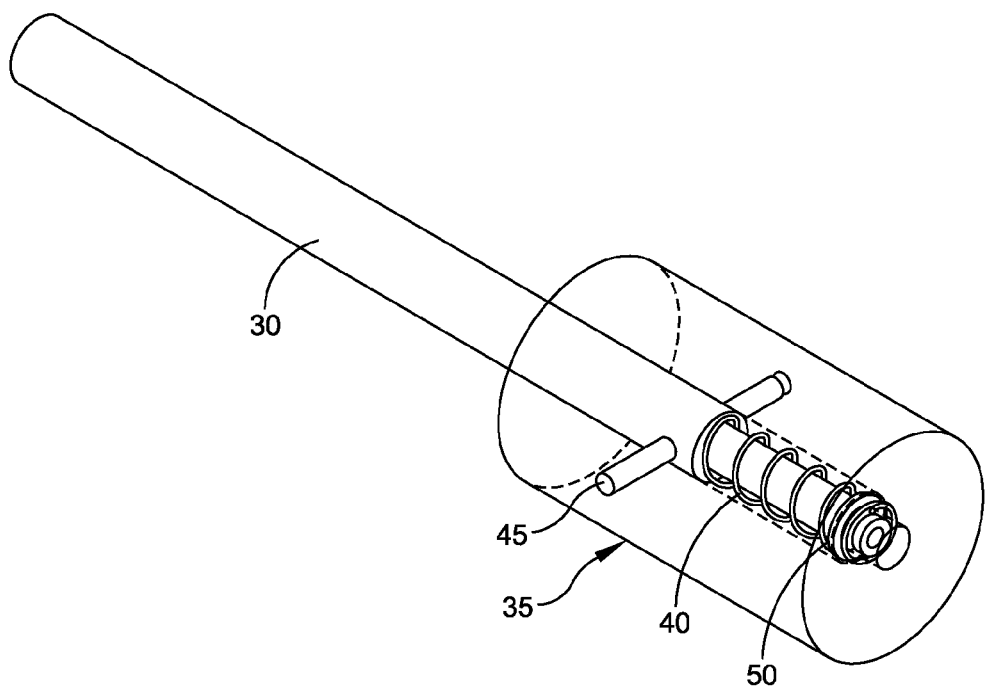
Figure 18A:
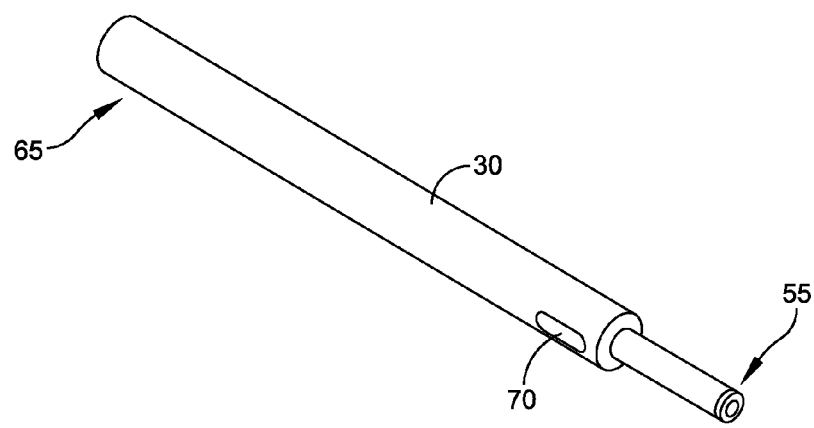
Figure 18B:
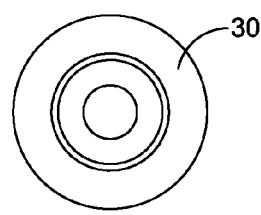
Figure 18C:
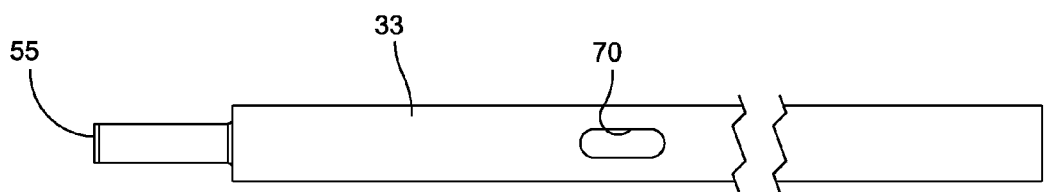
Figure 19A:
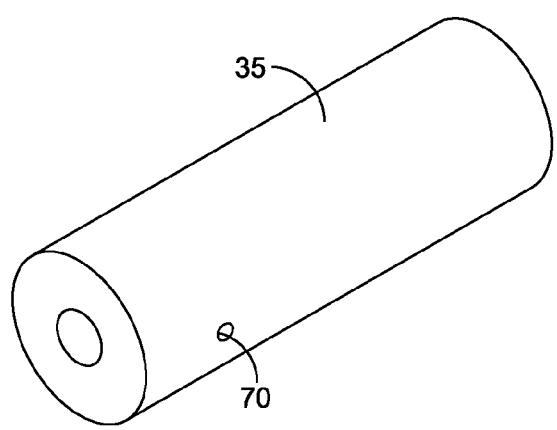
Figure 19B:
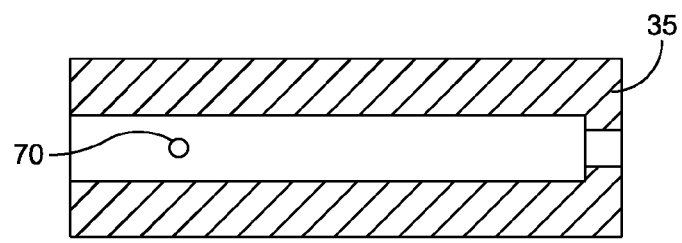
Figure 19C:
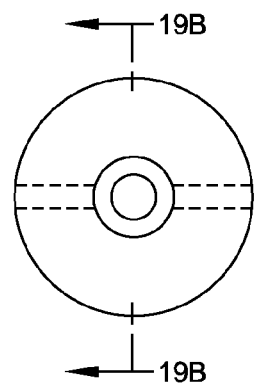

FIGS. 17A, 17B illustrate various views of one exemplary embodiment of plunger 30, handle 35, spring 40, retaining pin 45, shim 50, and slot 70. FIGS. 18A-18C illustrate various views of an exemplary embodiment of an exemplary embodiment of plunger 30. FIGS. 19A-19C illustrate various views of an exemplary embodiment of handle 35.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A constant force compression tool for measuring a given volume of a compressible material at a desired compressive pressure, the tool comprising:
    a plunger having a first end and a second end in opposition to one another, the first end having a surface configured to compress the compressible material;
    a handle having a passageway receiving the plunger between the first end and the second end;
    a biasing member in communication with the plunger and the handle so as to provide a biasing force between the plunger and the handle; and
    a retaining element in communication with the plunger and the handle so as to prevent the plunger from disengagement with the handle;
    wherein the plunger, the handle, and the biasing member are coordinated with a measurement tube to (1) provide a desired compressive pressure to the compressible material, and (2) indicate a given volume of the compressible material.

2. The tool of claim 1, wherein the plunger having a ring at the second end, the ring configured to identify an appropriate measured volume of the compressible material, and wherein the handle includes a portion to index the ring of the plunger.

3. The tool of claim 1, wherein the biasing member is a spring.

4. The tool of claim 1, wherein the retaining element is a retaining pin.

5. The tool of claim 1, wherein the plunger, the handle, and the biasing member are configured with appropriate dimensions to interact with a tube so as to provide a measurement of a compressible material as determined by the positioning of the plunger contacting the compressible material.

6. A system for measuring a given volume of a compressible material at a desired compressive pressure, the system comprising:
    a measurement tube having a sidewall extending between a closed end and an open end; and
    a constant force compression tool including:
        a plunger having a first end and a second end in opposition to one another, the first end having a surface configured to compress the compressible material, and the second end having a ring configured to identify an appropriate measured volume of the compressible material, wherein the first end has a diameter and a length configured for disposition into the measurement tube through the open end toward the closed end;
        a handle having a passageway receiving the plunger between the first end and the second end, and a portion to index the ring of the plunger, wherein the handle has a stop sized to rest against the open end of the measurement tube;
        a biasing member in communication with the plunger and the handle so as to provide a biasing force between the plunger and the handle, wherein the biasing member has a fully compressed configuration extending the first end of the plunger an appropriate distance toward the closed end of the measurement tube so as to provide a predetermined amount of space within the measurement tube between the first end of the plunger and the closed end of the measurement tube; and
        a retaining element in communication with the plunger and the handle so as to prevent the plunger from disengagement with the handle;
    wherein the plunger, the handle, and the biasing member are configured for coordination with the measurement tube to (1) provide a desired compressive pressure to the compressible material, and (2) indicate a given volume of the compressible material.

7. The system of claim 6, wherein the plunger having a ring at the second end, the ring configured to identify an appropriate measured volume of the compressible material, and wherein the handle includes a portion to index the ring of the plunger.

8. The system of claim 6, wherein the biasing member is a spring.

9. The system of claim 6, wherein the retaining element is a retaining pin.

10. The system of claim 6, wherein the plunger, the handle, and the biasing member are configured with appropriate dimensions to interact with the tube so as to provide a measurement of a compressible material as determined by the positioning of the plunger contacting the compressible material.

11. A method of measuring a given volume of a compressible material at a desired compressive pressure, the method comprising:

selecting a measurement tube;

placing a compressible material into the measurement tube;

pressing a plunger of a constant force compression tool to dispose an end against the compressible material to provide a desired compressive pressure to the compressible material; and monitoring an indicator to determine if the plunger is disposed at a predefined distance within the measurement tube together with a full volume of the compressible material between the end of the plunger and the measurement tube so as to indicate a given volume of the compressible material based on the full volume of the compressible material.

12. The method of claim 11, wherein the step of pressing the plunger includes providing a predefined amount of force again the compressible material.

13. The method of claim 11, wherein the compressible material is a ground cancellous bone material.

14. The method of claim 11, further comprising determining the measurement tube and the constant force compression tool are sized to correspond to one another.

15. The method of claim 11, further comprising selecting the constant force compression tool with the plunger sized to provide a desired measurement of the compressible material with the measurement tube.

* * * * *